United States Patent [19]

Hendry et al.

[11] Patent Number: 4,705,796
[45] Date of Patent: Nov. 10, 1987

[54] USE OF 3-N-PHENYLACETYLAMINO-2,6-PIPERIDINEDIONE FOR TREATMENT OF NEUROPSYCHIATRIC DISORDERS

[75] Inventors: Lawrence B. Hendry; Ana H. Diamond; Bruce I. Diamond; Douglas E. Ewing, all of Augusta, Ga.

[73] Assignee: Stereochemical Genetics, Inc., Augusta, Ga.

[21] Appl. No.: 899,822

[22] Filed: Aug. 25, 1986

[51] Int. Cl.$^4$ .................................. A61K 31/445
[52] U.S. Cl. ........................................ 514/328
[58] Field of Search ............................ 514/328

[56] References Cited

U.S. PATENT DOCUMENTS 4,470,970  9/1984  Burzynski ................. 424/177
4,558,057  12/1985  Burzynski ................ 514/328

OTHER PUBLICATIONS

Burzynski et al., "Human Toxicology Studies on Oral Formulation of Antineoplaston A10" (Drugs Exptl. Clin. Res. 891–909, 1984).
Diamond et al., "Differentiation of Phenylethylamine (PE)-and Amphetamine (AMPH)-Induced Behaviors" (Neurobiology of the Trace Amines 375–388, 1984).
Ortmann et al., "Phenylethylamine–Induced Stereotypes in the Rat: a Behavioral Test System for Assessment of MAO-B Inhibitors" (Psychopharmacology 84:22–27.
Johnston, "Some Observations Upon a New Inhibitor of Monoamine Oxidase in Brain Tissue" (Biochemical Pharmacology 17:1285–1297, 1968).
Birkmayer et al., "Deprenyl Prolongs the Therapeutic Efficacy of Combined L–DOPA in Parkinson's Disease" (Advances in Neurology 40:475–481, 1984).
Diamond et al., "Neuropeptides and other Dopamine Modulators in the Extrapyramidal System" (Catecholamines: Basic & Clinical Frontiers 1620–1622, 1979).

Primary Examiner—Stanley J. Friedman
Attorney, Agent, or Firm—Arnold, White & Durkee

[57] ABSTRACT

Composition of 3-N-phenylacetylamino-2,6-piperdinedione is disclosed as useful in the treatment of neuropsychiatric disorders involving monoamine oxidase regulation. 3-N-phenylacetylamino-2,6-piperidinedione has been shown to be an effective and selective MAO type B inhibitor.

3 Claims, No Drawings

USE OF 3-N-PHENYLACETYLAMINO-2,6-PIPERIDINEDIONE FOR TREATMENT OF NEUROPSYCHIATRIC DISORDERS

BACKGROUND OF THE INVENTION

1. Field of the Invention

The present invention relates generally to chemical compositions and their use in the treatment of neuropsychiatric disorders. More particularly, the compositions comprise an amino acid derivative, 3-N-phenylacetylamino-2,6-piperidinedione (heretofore referred to as PAPD) useful in the treatment of neuropsychiatric disorders associated with monoamine oxidase regulation.

2. Background of the Invention

A need for new psychotropic agents arises from the toxicity and the limited efficacy of currently available compounds. Each class of psychotropic agents is plagued by side effects and/or toxic effects which limit their clinical utility: neuroleptics cause extrapyramidal syndromes and tardive dyskinesia; antidepressants cause atropinism and excess sedation; anxiolytics produce tolerance and sedation; and monoamine oxidase inhibitors alternatively cause hypotension or hypertensive crises. The limited effectiveness of existant psychotropics in treating selected patients with common neuropsychiatric disorders combined with these unwanted toxic effects produces a need for further psychotropic drug development.

A stereochemical model (U.S. Pat. No. 4,461,619, 1984) has already been developed to determine a priori both the biological activity and probable toxicity of a wide range of endogenous compounds and therapeutic agents. This list includes but is not limited to the following: sex hormones, thyroid hormones, glucocorticoids, mineralocorticoids, vitamins, antineoplastic agents, antibiotics, neurotransmitters and psychotropics. Other investigators have also been involved in finding novel psychotropic agents with two basic approaches: first, to improve existing compounds which presumably affect a neurotransmitter such as dopamine, serotonin, norepinephrine, GABA and/or acetylcholine; and second to develop new compounds which affect the above and peptide neurotransmitters such as endorphine, enkephalins, cholecystokinin, vasopressin, substance P and others.

3. Development of the Invention

Interest in developing effective and non-toxic agents, combined with a focus on peptides as possible new psychotropic agents, resulted in the discovery that an existing dipeptide agent PAPD fit in the stereochemical model in a way similar to existing psychotropics. Previous work with PAPD as an antineoplastic agent had demonstrated a lack of toxic effects. Moreover, clinical investigators noted both an elevation of mood and diminished need for analgesia in some cancer patients who were treated with PAPD. These clinical observations, combined with a fit of PAPD into a neurotransmitter/psychotropic model suggested that PAPD might be a dipeptide with psychotropic activity. The present applicants then postulated that PAPD might be an antipsychotic, antidepressant, anxiolytic and/or analgesic agent based on knowledge that substances with these various effects can elevate mood and/or reduce the need for analgesia.

Thereafter, an analysis of a PAPD was undertaken in vitro and in vivo beginning with antipsychotic (neuroleptic) and antidepressant activity. It was determined that PAPD lacked substantial neuroleptic activity based on both its inability to displace $H^3$-spiroperidol from rat caudate nucleus and inability to reverse apomorphine and amphetamine induced locomotor changes in rats. Investigation of PAPD's possible monoamine oxidase (MAO) inhibition by standard platelet analysis demonstrated a significant degree of MAO inhibition. The two distinct forms of the enzyme have been designated as type A (serotonin metabolizing and clorgyline sensitive) and type B (phenyethylamine metabolizing and clorgyline insensitive). Based on the stereochemical model, it was predicted that PAPD's effect on MAO type B would be greater than its effect on MAO type A. In vitro data has substantiated this prediction.

A large number of compounds are inhibitors of MAO, and the elevation of mood by some of these agents is believed to be related to the accumulation of one or more of these biogenic amines in the synaptic cleft. The clinical utility of these compounds is related to the treatment of depression, panic disorders and Parkinson's disease. However, this utility is hindered because of serious untoward effects, particularly the hypertensive crisis that may result following the ingestion of tyramine containing foods by patients taking certain MAO inhibitors. Because of the existence of two catalytic varieties of MAO which can be specifically inhibited by certain drugs, it is conceivable that the unwanted side effects may be eliminated by the use of specific and selective inhibitors.

In summary, the search for a new, effective, non-toxic psychotropic compound began with the investigation of an existing dipeptide analog, PAPD. PAPD fit into a stereochemical model like other known psychotropic agents. In vitro and in vivo analyses have shown PAPD to be an MAO inhibitor with inhibition of MAO type B greater than that for MAO type A.

Because the main clinical toxicity (hypertensive crisis from ingestion of tyramine) may relate to MAO type A inhibition, PAPD shows promise as a potentially clinically effective, non-toxic, relatively selective MAO type B inhibitor. At present there is one agent commercially available in the United States which is a relatively selective MAO type B inhibitor but it is used as an antihypertensive. A selective MAO type B inhibitor is of great clinical utility because of the potential for lack of a need for dietary restriction of tyramine containing food. This dietary restriction lisits the clinical utility of existing MAO inhibitors because of the patient's and physician's reluctance to risk toxicity by accidental ingestion of common foods as well as serious drug-drug interactions with conventional MAO inhibitors.

SUMMARY OF THE INVENTION

PAPD provides a method for inhibiting monoamine oxidase type B activity in a mammalian host by the administration of an effective monoamine oxidase inhibiting amount of PAPD or its pharmaceutically effective salts. By utilization of the claimed method, PAPD is effective to treat various neuropsychiatric disorders evidenced by depression, panic attacks and/or Parkinson's disease.

DESCRIPTION OF THE PREFERRED EMBODIMENT

The invention is described below in terms of preferred embodiments known at the time of this application. These embodiments represent the best mode contemplated for preparing the antidepressant and antiparkinsonian compositions and their method of use.

The particular amino acid derivative used in the present composition, PAPD, may be extracted from natural body fluids or be prepared synthetically by combining the amino acid, L-glutamine, and phenylacetyl chloride. For use as an antidepressant or antiparkinsonian composition, the compound PAPD is preferably prepared synthetically as described in prior U.S. Pat. Nos. 4,470,970 and 4,558,057 herein incorporated by reference.

IN VITRO DATA

PAPD was investigated for its effects on MAO B activity in vitro using human platelets and on MAO A and B in human and rat brain tissue. Radiolabeled phenylethylamine ($^{14}$C-PEA) was used as the substrate for MAO B activity while radiolabeled 5-hydroxytryptamine ($^{14}$C-5HT) was used as the substrate for MAO A activity. Standard type A MAO inhibitors (clorgyline) affect selectively 5HT metabolism whereas type B MAO inhibitors such as deprenyl affect selectively PEA breakdown. All commercially available MAO inhibitors on the U.S. market that are used for depression and related psychiatric disorders inhibit both 5HT and PEA activity.

EXAMPLE 1

The effect of PAPD on platelet MAO B activity was studied in vitro from blood collected from normal volunteers. 5 ml of blood were collected in a Venojet tube containing EDTA, gently mixed, and immediately chilled on ice. Tubes were centrifuged at 200 g in a refrigerated centrifuge at 7 degrees C. The supernatant (platelet rich plasma) was removed into plastic tubes and centrifuged at 2000 g for 10 minutes. The platelet pellet was resuspended in 5.0 ml of 0.1 M phosphate buffer with pH 7.4 by sonication. The suspension was divided into aliquots and frozen at -80 degrees C. or used for assay immediately.

Both pargyline (a MAO B selective inhibitor) and PAPD inhibited human platelet MAO B activity. There was a linear inhibition with increasing concentration of PAPD in the range of 0.1 to 1.0 mM above which maximal inhibition (100%) was reached. The experiment was conducted on platelets obtained from 6 subjects in duplicate enzyme assays. The concentration of drug that inhibits MAO enzyme activity by 50% (IC$_{50}$) was determined by computer analysis. The mean IC$_{50}$ values for PAPD inhibition of platelet MAO B activity was $63.8 \times 10^{-6}$M with a standard deviation of $34.5 \times 10^{-6}$. Pargyline also inhibited platelet MAO and was more potent in doing this. Thus, these results support the notion that PAPD is a MAO B inhibitor which is less potent than pargyline. To get equivalent inhibition to that of pargyline, more PAPD would have to be given on a milligram basis.

EXAMPLE 2

The MAO A and B inhibitory properties of PAPD were also studied in human and rat brains in vitro. Human and rat caudate nuclei were homogenized in 0.32M sucrose to yield a 1% homogenate (1 g/100 ml). Aliquots of this homogenate corresponding to 200 micrograms of protein were used in the assay as the enzyme source.

MAO activity was determined with C$^{14}$ PEA as substrate using a modified method described originally by Wurtman and Axelrod (Biochem. Pharmacol. 12, 1439-1440 (1963)). In standard assay procedure, aliquots of homogenate containing 100.0 micrograms of protein (protein concentrations in the suspension were determined by the method of Lowry et al. (J. Biol. Chem. 193, 265-275 (1951)) were incubated in a total volume of 0.2 ml with the substrate soluted in 0.1M phosphate buffer pH 7.4 containing 0.9% KCL. Fifty nCi of C$^{14}$ PEA were diluted with nonlabeled PEA to yield a 15 micromolar working solution. Tubes were incubated 30 minutes at 37 degrees C. in a water bath (constantly shaken) and the reaction was terminated by adding 25 microliters of 70% perchloric acid. Reaction tubes were chilled immediately. 5.0 ml of toluene were added to each tube and they were shaken for an additional two minutes. Tubes were centrifuged for 20 minutes at 1000 g. 3.5 ml of the organic phase were removed and upon addition of the scintillation fluid the activity was counted in a scintillation counter. Activity is expressed as DPM's/100 microgram of protein/30 minutes.

MAO type A was assayed in the brain homogenate using $^{14}$C-5-hydroxytryptamine (5HT) as a substrate. The stock radioactive solution was diluted with non-radioactive 5HT to yield a 0.25 mM work solution. Following a 1:10 dilution, this substrate was incubated with aliquots of brain homogenates containing 0.2 mg protein for 30 min. The incubation was stopped by the addition of 72% perchloric acid. The separation of the oxidative metabolites from the unoxidized amine was achieved by toluene extraction. The phases were separated by centrifugation at 1000 g for 20 minutes and an aliquot of 3.5 ml of the upper phase was placed in a scintillation vial to which 8 ml of scintillation fluid was added and the radioactivity was counted by liquid scintillation counting.

Each assay was run in duplicate and experiments were repeated three times. The specificity of MAO inhibitors was studied in the same rat or human brain preparations which were incubated with either $^{14}$C-5HT or $^{14}$C-PEA as the substrate. Inhibition curves were generated by incubating the brain preparations with radiolabeled substrate in the presence of increasing amounts of a given drug. The IC$_{50}$ values were calculated by computer analysis.

PAPD inhibited rat brain MAO A and B activity. The IC$_{50}$ value for the A type was $93.3 \times 10^{-6}$M with a standard deviation (SD) of $\pm 6.0$ and the B type was $8.0 \times 10^{-6}$M with a SD of $\pm 2.1$. These results demonstrate that PAPD preferentially inhibits the MAO type B enzyme and does so at concentrations 10 times less than needed to affect MAO A activity. In human brain tissue the IC$_{50}$ value for PAPD effects on MAO A activity was $138.6 \times 10^{-6}$M $\pm$ SD of 15.1 and for MAO B activity was $19.9 \times 10^{-6}$ M $\pm$ SD of 3.7. Thus in human brain tissue, PAPD was five times more selective for type B MAO activity. Tranylcypromine and phenelzine, two MAO inhibitors without specificity for A or B type enzyme, had IC$_{50}$ values for type B MAO in human brain of 0.2 and $0.1 \times 10^{-6}$M. Although these drugs are two orders of magnitude more potent than PAPD, they are not selective for the B type MAO and reflect only differences in milligram potency required for enzyme inhibition.

IN VIVO DATA

Various laboratory analyses have revealed that PAPD is a MAO inhibitor and has favorable effects as an antidepressant, antipanic and antiparkinsonian drug. Studies using the drug were conducted in vitro and in laboratory rats.

Studies in laboratory rats which were housed individually in a controlled environment were also done. Powdered PAPD was dissolved and the pH adjusted with 1N HCL. The final pH of the solution was 7.4. The drug was injected intraperitoneally in a concentration of 0.1 ml/100 grams.

PAPD was investigated in various animal models where PEA is known to exert specific effects as a substrate of MAO type B. PEA produces amphetamine-like stereotypies in animals, and inhibitors of MAO B (pargyline and deprenyl) increase and prolong these behaviors. Basically, potentiation of PEA induced stereotype behavior in rats, PEA induced rotations in unilateral nigral lesioned rats and PEA reversal of reserpinized rats were studied.

EXAMPLE 3

PEA induced stereotype behavior was assessed in rats (six per group) pretreated with varying doses of either saline, deprenyl, clorgyline and PAPD. Pretreatment usually was one hour prior to 50 mg/kg of PEA. In certain studies pretreatment times varied between 1 and 24 hours. Animals were rated tor stereotype behavior every 5 minutes for 30 seconds after PEA administration in wire mesh cages. Stereotype behavior was rated in two ways. The first included the presence or absence of forepaw padding and continuous sniffing which has been associated with MAO B inhibitors and PEA administration. The number of animals showing this syndrome for at lease one observation period during the 20 minute test period following PEA was counted. The second way stereotype behavior was quantitated was with the use of a rating scale where higher numbers reflect more intense stereotype behavior. The mean of every 5 minute rating for 30 minutes was used as a total score. Also duration of stereotype behavior was noted.

After PEA administration (50 mg/kg) no stereotype behavior was observed. However, rats showed exophthalmus, locomotor hyperactivity, rearing, piloerection with normal sniffing. Rats never showed forepaw padding, continuous stereotyped sniffing or headbobbing. Pretreatment one hour prior to PEA with the B MAO inhibitor, deprenyl, changed the PEA behavior to forepaw padding with continuous sniffing and headweaving that lasted for 60 minutes. Five mg/kg of deprenyl produced this behavior in 50% of animals whereas 100% of animals had this behavior with 10 mg/ kg. There was no other stereotype behavior observed with deprenyl pretreatment.

Pretreatment with the type A MAO inhibitor, clorgyline, produced dose dependen effects on PEA behavior. At 10 mg/kg, clorgyline one hour prior to PEA produced forepaw padding, sniffing, headweaving and retropulsion in 100% of the animals. In contrast, 5 mg/kg of clorgyline did not produce this syndrome in PEA treated rats. However, it did produce stereotyped headbobbing at this dose. The effects of both doses of clorgyline lasted 30 minutes. At 50 and 100 mg/kg of PAPD pretreatment no effects on PEA behavior were noticed. However, the 200 and 400 mg/kg dose of PAPD produced forepaw padding with continuous sniffing as well as headweaving in 100% of the animals. This lasted for 45 to 50 minutes. Other stereotype behavior noted with this treatment was headbobbing. PEA produced forepaw padding with continuous sniffing as well as headweaving in 100% of animals pretreated one and two hours prior with PAPD. This behavior lasted 45 to 55 minutes respectively. After 4 and 24 hours of PAPD administration, 50% and 66% of the animals displayed this behavior which lasted 30 minutes in both groups.

EXAMPLE 4

The rotational behavior in unilateral substantia nigra 6-hydroxydopamine lesioned rats is a classical model to determine dopasine agonist type drugs. Ungerstedt, U., *Acta Physiologica Scandanavia* 367:69-93 (1971). Rats were anesthesized with pentobarbital (37 mg/kg; i.p.) and placed in a David Korf stereotaxic apparatus. The skull was exposed and a hole drilled 5.3 mm posterior and 2.6 mm lateral to Bregma. A Hamilton microliter syringe filled with 4 microliters of 6-hydroxydopamine (8 micrograms) and ascorbic acid (2 micrograms) was lowered 7.6 mm through the hole. The solution was injected at a rate of 1 microliter per minute for 4 minutes. The needle was left in place an additional minute before being removed. The rats were sutured and returned to their cage. After 10 days, animals were tested with apomorphine (1 mg/kg) and amphetamine (3.7 mg/kg). If the lesion was successful, animals were found to rotate away from the lesioned side in response to the direct dopamine receptor agonist apomorphine and rotate to the side of the lesion in response to drugs that release presynaptic dopamine such as amphetamine and PEA. Animals that did not rotate to either apomorphine or amphetamine were discarded. At the conclusion of the study, brains from some animals were removed and the nigral lesion confirmed by light microscopy and cresyl violet stain. Twenty-one days following the lesion, four rats per group were administered PEA (50 mg/kg) and baseline turning to the lesioned side quantitated. During the following days rats were given PAPD (50–500 mg/kg, i.p.) to ascertain if it itself produced any turning. Nigral lesioned rats were pretreated with either deprenyl (10 mg/kg) or PAPD (50–500 mg/kg) one hour prior to PEA (50 mg/kg) and turning to the side of the lesion counted for one minute every ten minutes during the half hour following PEA administration.

PEA induced ipsilateral turning in 6-hydroxydopamine unilateral nigral lesioned rats. Duration of these rotations lasted for 30 minutes. Treatment with the type B MAO inhibitor deprenyl doubled the number of ipsilateral turns induced by PEA and increased the duration of PEA rotations in these animals. 50, 100 and 150 mg/kg of PAPD when administered one hour before PEA, did not affect the number or duration of PEA rotations. However, the 200 mg/kg dose like deprenyl, increased the number and duration of PEA rotations.

EXAMPLE 5

In a third study, the ability of MAO inhibitors to potentiate the reversal of reserpine symptoms by PEA (50 mg/kg, i.p.) was studied in groups of six rats each. In this paradigm, rats were pretreated with reserpine (10 mg/kg, i.p.) 18 hours prior to PEA administration.

The ability of PEA to antagonize the akinesia induced by reserpine was measured as latency to reversal of akinesia and duration of reversal. Six groups of reserpinized rats were treated one hour prior to PEA with either saline, pargyline (50 mg/kg), clorgyline (5 mg/kg) or PAPD (50, 100 and 200 mg/kg).

Reserpine-induced akinesia in rats was reversed in less than five minutes by PEA administration. The animals were active and walking around for 30 minutes. When the type A MAO inhibitor clorgyline was given one hour prior to PEA animals were able to move in less than five minutes. However, they were not as active as PEA control animals and displayed serotonin type behavior such as splayed hind legs, myoclonic jerks and headweaving. This lasted for 45 minutes. The type B MAO inhibitor pargyline, when given prior to PEA, reversed the reserpine-induced akinesia in less than five minutes. These animals were active and displayed increased locomotion for 45 minutes. The effects of PAPD pretreatment on the reversal of the reserpine akinesia by PEA displayed an unusual dose response curve. 50 and 100 mg/kg of PAPD antagonized the reversal induced by PEA, whereas 200 mg/kg potentiated the duration of PEA's reversal of akinesia. The latency to reversal of akinesia by PAPD was less than five minutes. These animals were active with increased locomotion for 50 minutes. However, interspersed with this locomotor activity were the serotonin behaviors of headweaving and tremors.

What is claimed is:

1. A method of inhibiting monoamine oxidase type B activity in a mammalian host affected by neuropsychiatric disorders comprising administering internally to said host an effective monoamine oxidase inhibiting amount of 3-N-phenylacetylamino-2,6-piperidinedione or pharmaceutically effective salts thereof.

2. A method of treating neuropsychiatric disorders that involve monoamine oxidase regulation comprising administering by injection to a mammalian host affected with neuropsychiatric disorders an effective monoamine oxidase inhibiting amount of 3-N-phenylacteylamino-2,6-piperidinedione or its pharmaceutically effective salts.

3. The method of claim 2 wherein the effective amount of 3-N-phenylacetylamino-2,6-piperidinedione is effective to treat neuropsychiatric disorders evidenced by depression, panic attacks and Parkinson's disease.

* * * * *